(12) United States Patent
Nygaard

(10) Patent No.: US 8,416,403 B2
(45) Date of Patent: Apr. 9, 2013

(54) METHOD AND SYSTEM FOR HIGH-SPEED, HIGH-RESOLUTION 3-D IMAGING OF MANUFACTURED PARTS OF VARIOUS SIZES

(75) Inventor: Michael G. Nygaard, Fenton, MI (US)

(73) Assignee: GII Acquisitiom, LLC, Davisburg, MI (US)

( * ) Notice: Subject to any disclaimer, the term of this patent is extended or adjusted under 35 U.S.C. 154(b) by 364 days.

(21) Appl. No.: 12/915,533

(22) Filed: Oct. 29, 2010

(65) Prior Publication Data

US 2012/0105429 A1    May 3, 2012

(51) Int. Cl.
*G01N 21/00* (2006.01)

(52) U.S. Cl.
USPC ............................ 356/239.4; 356/601

(58) Field of Classification Search ............... 356/239.4, 356/601
See application file for complete search history.

(56) References Cited

U.S. PATENT DOCUMENTS

| | | | |
|---|---|---|---|
| 2,444,457 A | 7/1948 | Marks et al. | |
| 3,013,467 A | 12/1961 | Minsky | |
| 4,547,674 A | 10/1985 | Pryor et al. | |
| 4,778,252 A | 10/1988 | Filho | |
| 4,923,066 A | 5/1990 | Ophir et al. | |
| 4,938,489 A | 7/1990 | Nemirovsky | |
| 4,970,401 A | 11/1990 | Sadeh et al. | |
| 5,024,529 A | 6/1991 | Svetkoff et al. | |
| 5,098,031 A | 3/1992 | Hitomi | |
| 5,136,157 A * | 8/1992 | Apter et al. ............. | 250/223 B |
| 5,175,428 A * | 12/1992 | Agerskov et al. ....... | 250/223 B |
| 5,546,189 A | 8/1996 | Svetkoff et al. | |
| 5,617,209 A | 4/1997 | Svetkoff et al. | |
| 5,815,275 A | 9/1998 | Svetkoff et al. | |
| 6,098,031 A | 8/2000 | Svetkoff et al. | |
| 7,403,872 B1 | 7/2008 | St. Onge et al. | |

(Continued)

FOREIGN PATENT DOCUMENTS

WO    2005022076 A2    3/2005

*Primary Examiner* — Roy M Punnoose
(74) *Attorney, Agent, or Firm* — Brooks Kushman P.C.

(57) ABSTRACT

A method and system for high-speed, high-resolution 3-D imaging of manufactured parts of various sizes at an imaging station having a measurement axis are provided. The part has a 3-D end surface and a length, a width and a part axis defined as being central to the part and parallel to its length. The system includes apparatus having a central axis substantially parallel to the measurement axis and a plurality of members having open and closed positions. The members have holding faces which are substantially equidistant from the central axis during movement between the positions to align a part disposed between the holding faces at the station so that the part axis is substantially parallel to the measurement and central axes. The holding faces releasably hold the aligned part in a holding position between the positions. The system further includes an actuator for moving the apparatus so that the end surface moves in a plane substantially perpendicular to the measurement axis. The system still further includes a controller for controlling the actuator to move the end surface along a 2-D trajectory within the plane. The system further includes at least one sensor for emitting a beam of energy along the measurement axis onto the end surface during movement of the end surface along the 2-D trajectory to obtain reflected energy and for sensing at least a portion of the reflected energy to obtain an output. The system still further includes a processor for processing the output to obtain information related to the end surface of the part.

23 Claims, 3 Drawing Sheets

U.S. PATENT DOCUMENTS

| | | | |
|---|---|---|---|
| 2006/0140470 A1* | 6/2006 | Watanabe | 382/142 |
| 2008/0056556 A1* | 3/2008 | Eller et al. | 382/142 |
| 2009/0103107 A1 | 4/2009 | Nygaard | |
| 2009/0103112 A1 | 4/2009 | Nygaard | |

* cited by examiner

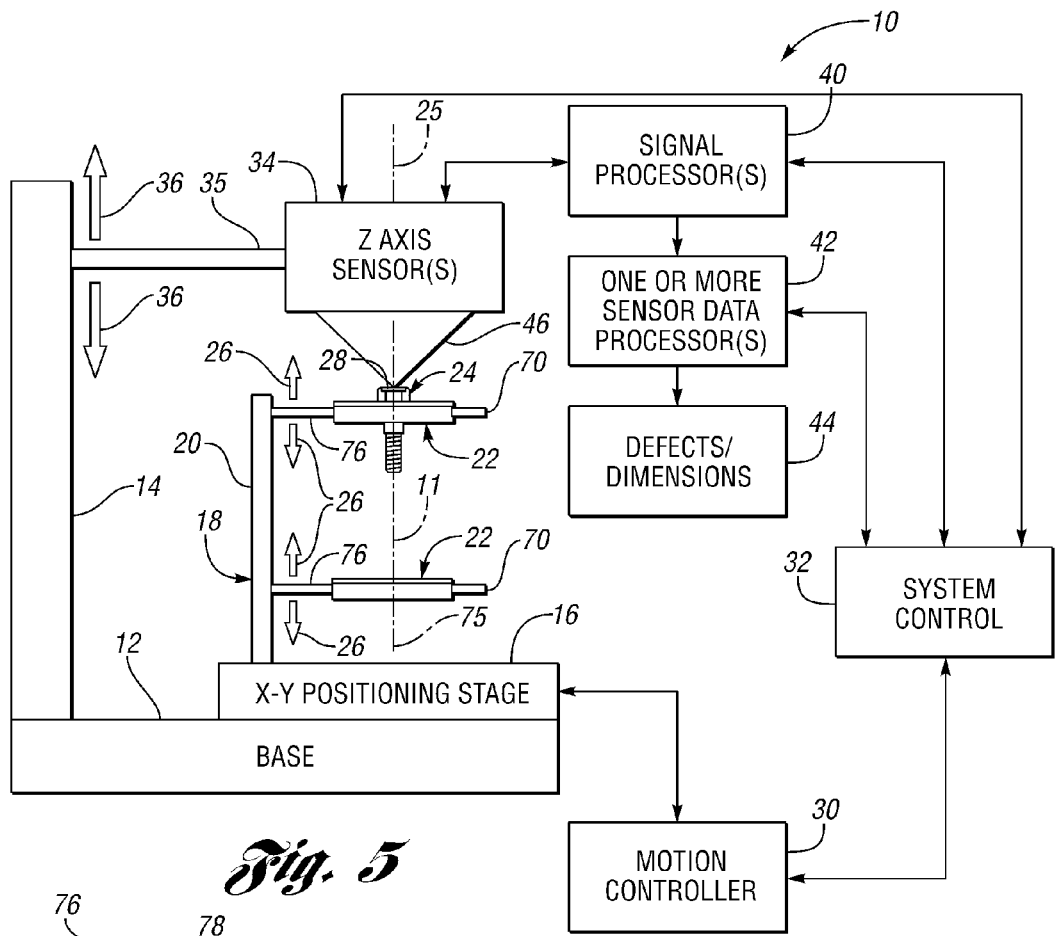
Fig. 5
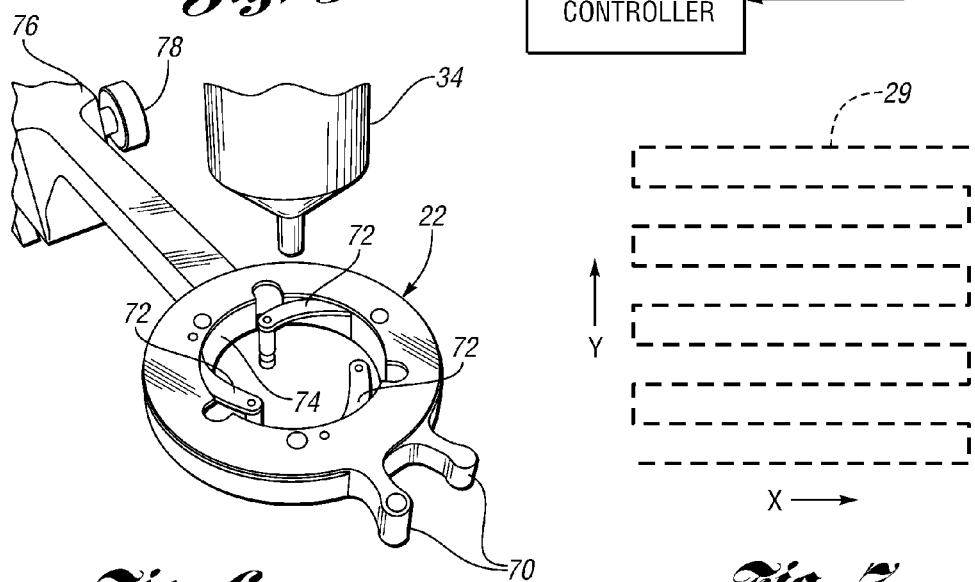
Fig. 6
Fig. 7

METHOD AND SYSTEM FOR HIGH-SPEED, HIGH-RESOLUTION 3-D IMAGING OF MANUFACTURED PARTS OF VARIOUS SIZES

CROSS-REFERENCE TO RELATED APPLICATIONS

This application is filed on the same day as commonly-owned U.S. patent application entitled "Method And System For Centering And Aligning Manufactured Parts Of Various Sizes At An Optical Measurement Station" (U.S. Ser. No. 12/915,579).

This application is related to commonly-owned U.S. patent applications entitled "System For Indirectly Measuring A Geometric Dimension Related To An Opening In An Apertured Exterior Surface Of A Part Based On Direct Measurements Of The Part When Fixtured At A Measurement Station" filed Mar. 27, 2009 (U.S. Ser. No. 12/412,909); and "Method And System For Automatically Inspecting Parts And For Automatically Generating Calibration Data For Use In Inspecting Parts" filed Feb. 12, 2010 (U.S. Ser. No. 12/704,863).

This application is also related to the following commonly-owned U.S. patent applications which were filed on Sep. 19, 2008:
1) Non-Contact Method And System For Inspecting Parts (U.S. Ser. No. 12/233,829);
2) Method And System For Inspecting Parts Utilizing Triangulation (U.S. Ser. No. 12/233,831); and
3) Method For Precisely Measuring Position Of A Part To Be Inspected At A Part Inspection Station (U.S. Ser. No. 12/233,821).

This application is further related to the following commonly-owned U.S. patent applications which were filed on Oct. 23, 2007:
1) Method And System For Optically Inspecting Parts (U.S. Ser. No. 11/977,117);
2) Method For Estimating Thread Parameters Of A Part (U.S. Ser. No. 11/977,097) (now U.S. Pat. No. 7,633,046);
3) Optical Modules And Method Of Precisely Assembling Same (U.S. Ser. No. 11/977,102) (now U.S. Pat. No. 7,633,634);
4) Method And Inspection Head Apparatus For Optically Measuring Geometric Dimensions Of A Part (U.S. Ser. No. 11/977,010);
5) Apparatus For Quickly Retaining And Releasing Parts To Be Optically Measured (U.S. Ser. No. 11/977,091);
6) Calibration Device For Use In An Optical Part Measuring System (U.S. Ser. No. 11/977,114); and
7) Method And System For Generating Calibration Data For Use In Calibrating A Part Inspection System (U.S. Ser. No. 11/975,977).

This application is further related to commonly-owned U.S. patent application entitled "Profile Inspection System For Threaded And Axial Components" filed Aug. 25, 2006 and having U.S. Ser. No. 11/510,402 (now U.S. Pat. No. 7,684,054).

BACKGROUND OF THE INVENTION

1. Field of the Invention

The present invention relates to methods and systems for high-speed, high-resolution 3-D imaging of manufactured parts of various sizes, such as threaded fasteners and cartridge cases.

2. Background Art

Inspection of defects on small arms ammunition cartridges and cases is a vital aspect in the manufacturing process, allowing for maintenance of a high level of quality and reliability in the munitions industry. Standards have been developed and applied by manufacturers for many years to assist in classifying various types of defects. Alternatively, a military standard is used such as that introduced in 1958 by the US Department of Defense, MIL-STD-636. For small arms ammunition calibers up to .50, this standard serves to evaluate and illustrate a practical majority of defects assembled as a result of extensive surveys covering all the small arms ammunition manufacturing facilities in the United States.

FIGS. 1a and 1b are side and bottom schematic views, respectively, of a .50 caliber case. As explained in the above-noted military standard, a case is to be counted as a defective because of a split case if the cartridge case shows a definite separation of the metal entirely through the case wall. A case is to be classified as either a "major" or "critical" defect depending on the location of split. A split in the neck (I), taper (S) or case (J) position shall be counted as a "major" defect when no loss of powder occurs; and as a "critical" defect when loss of powder occurs. A split in the case (K), groove (L) or head (M) position shall be counted as a "critical" defect.

FIGS. 1c and 1d are side and bottom schematic views, respectively, of a .30 caliber case. As noted above, a case is to be counted as a defective because of a split case if the cartridge case shows a definite separation of the metal entirely through the case wall. A case is to be classified either as a "major" or "critical" defective depending on location of split. A split in the (I) or (J) position shall be counted as a "major" defect when no loss of powder occurs; and as a "critical" defect when loss of powder occurs. A split in the (K), (L) or (M) position shall be counted as a "critical"defect.

FIGS. 1e and 1f are side and bottom schematic views, respectively, of a .45 caliber case. Again, as noted above, a case is to be counted as defective because of a split case if the cartridge case shows a definite separation of the metal entirely through the case wall. A case is to be classified either as a "major" or "critical" defective depending on the location of the split. A split in the (I) or (J) position shall be counted as a "major" defect when no loss of powder occurs. A split in the (K), (L) or (M) position shall be counted as a "critical" defect.

U.S. Pat. No. 4,923,066 discloses an automatic visual inspection system for small arms ammunition which sorts visual surface flaws at high speed according to established standards. The system comprises interface apparatus for receiving a supply of ammunition cartridges and providing each cartridge with a predetermined orientation, conveying apparatus for locating each of the cartridges for inspection in at least one inspection station, apparatus for imaging selected areas of each cartridge to provide video surface feature data associated therewith, and apparatus for processing the video surface feature data to detect the presence of a predetermined set of characteristics and provide output signals in accordance therewith, the conveying apparatus being operated to sort each of the inspected cartridges in accordance with the output signals. Since many surface flaws look the same in two dimensions, such as scratches and splits or acid holes and stains, special lighting of the cartridges is used so that discrimination between them can be achieved on the basis of off-specular reflections.

U.S. Pat. No. 7,403,872 discloses a method and system for inspecting manufactured parts, such as cartridges and cartridge cases, at a plurality of inspection stations including a circumference vision station and primer and mouth vision stations.

PCT Patent Application No. WO 2005/022076 A2 discloses a part inspection apparatus including two embodiments of a self-centering clamp which drops parts to be inspected.

As described in U.S. Pat. No. 6,098,031, triangulation is the most commonly used 3-D imaging method and offers a good figure of merit for resolution and speed. U.S. Pat. Nos. 5,024,529 and 5,546,189 describe the use of triangulation-based systems for inspection of many industrial parts, including shiny surfaces like pins of a grid array. U.S. Pat. No. 5,617,209 shows a scanning method for grid arrays which has additional benefits for improving accuracy. The method of using an angled beam of radiant energy can be used for triangulation, confocal or general line scan systems. Unfortunately, triangulation systems are not immune to fundamental limitations like occlusion and sensitivity to background reflection. Furthermore, at high magnification, the depth of focus can limit performance of systems, particularly edge location accuracy, when the object has substantial relief and a wide dynamic range (i.e. variation in surface reflectance). In some cases, camera-based systems have been combined with triangulation systems to enhance measurement capability.

Confocal imaging, as originally disclosed by Minsky in U.S. Pat. No. 3,013,467, is similar to computerized tomography where slices in depth are sequentially acquired and the data is used to "reconstruct" a light scattering volume. In principle, an image is always formed of an object at a focal plane as taught in elementary physics, but over a region of depth there are an infinite number of planes which are out of focus yet return energy. That is to say that the lens equation for image formation is based on an idealization of an "object plane" and "image plane."

In the case of conventional confocal imaging, the slices are determined from the in-focus plane, and out-of-focus light (in front and back of the focal plane) is strongly attenuated with a pinhole or slit. Typical confocal systems use fine increments for axial positioning for best discrimination between adjacent layers in depth, for example, semi-transparent biological samples. However, the method need not be restricted to the traditional transparent or translucent objects, but can be applied both as a depth measurement tool and image enhancement method using reflected light for contrast improvement through stray light rejection. As with any method, there are advantages and disadvantages.

U.S. Pat. No. 5,098,031 discloses a versatile method and system for high-speed, 3-D imaging of microscopic targets. The system includes confocal and triangulation-based scanners or subsystems which provide data which is both acquired and processed under the control of a control algorithm to obtain information such as dimensional information about the microscopic targets which may be "non-cooperative." The "non-cooperative" targets are illuminated with a scanning beam of electromagnetic radiation such as laser light incident from a first direction. A confocal detector of the electromagnetic radiation is placed at a first location for receiving reflected radiation which is substantially optically collinear with the incident beam of electromagnetic radiation. The triangulation-based subsystem also includes a detector of electromagnetic radiation which is placed at a second location which is non-collinear with respect to the incident beam. Digital data is derived from signals produced by the detectors.

U.S. Pat. No. 5,815,275 discloses triangulation-based 3-D imaging using an angled scanning beam of radiant energy.

Published U.S. Patent Applications 2009/0103107 and 2009/0103112 disclose part inspection using a profile inspection subsystem and triangulation.

U.S. Pat. Nos. 2,444,457; 4,778,252 and 4,938,489 disclose self-centering holders for optical elements.

Other U.S. patents related to the invention include U.S. Pat. Nos. 4,547,674 and 4,970,401.

SUMMARY OF THE INVENTION

An object of the present invention is to provide an improved method and system for high-speed, high-resolution 3-D imaging of parts and, in particular, of 3-D end surfaces of manufactured parts of various sizes, such as threaded fasteners and cartridge cases.

In carrying out the above object and other objects of the present invention, a method of high-speed, high-resolution 3-D imaging of manufactured parts of various sizes at an imaging station having a measurement axis is provided. Each part has a 3-D end surface and a length, a width and a part axis defined as being central to the part and parallel to its length. The method includes aligning a part to be imaged at the station so that the part axis is substantially parallel with the measurement axis. The method further includes releasably holding the aligned part. The method still further includes scanning the end surface of the held part with a beam of energy along the measurement axis to obtain reflected energy. The method further includes sensing at least a portion of the reflected energy to obtain an output. The method still further includes processing the output to obtain information related to the end surface of the part. The method further includes generating control signals to control the step of scanning.

The step of scanning may include the steps of directing the beam of energy along the measurement axis and controllably moving the end surface relative to the beam along a 2-D trajectory in a plane substantially perpendicular to the part axis wherein the part axis is substantially perpendicular to the plane during the step of scanning.

The part may be threaded.

The part may be a threaded fastener having a recess in the end surface for accommodating a driver.

The threaded fastener may have a shank and the shank of the fastener may be releasably held during the step of holding.

The part may include a cartridge case having a mouth end and a primer end.

The end surface may be located at the primer end and the information may indicate at least one of a split, a crack, flash hole presence, primer absence, a cocked primer, primer pocket diameter, and an inverted primer.

The end surface may be located at the mouth end and the information may indicate at least one of a split, a fold, a dent, an out-of-round condition, inner diameter and outer diameter.

The beam may be a laser beam and the energy may be electromagnetic energy.

The step of sensing may be performed with a triangulation-based sensor.

The step of sensing may be performed with a confocal sensor.

Further in carrying out the above object and other objects of the present invention, a system for high-speed, high-resolution 3-D imaging of manufactured parts of various sizes at an imaging station having a measurement axis is provided. Each part has a 3-D end surface and a length, a width and a part axis defined as being central to the part and parallel to its length. The system includes apparatus having a central axis substantially parallel to the measurement axis. The apparatus has a plurality of members having open and closed positions.

The members have holding faces which are substantially equidistant from the central axis during movement between the open and closed positions to align a part disposed between the holding faces at the station so that the part axis is substantially parallel with the measurement and central axes. The system further includes an actuator for moving the apparatus so that the end surface moves in a plane substantially perpendicular to the measurement axis. The system still further includes a controller for controlling the actuator to move the end surface along a 2-D trajectory within the plane. The system further includes at least one sensor for emitting a beam of energy along the measurement axis onto the end surface during movement of the end surface along the 2-D trajectory to obtain reflected energy and for sensing at least a portion of the reflected energy to obtain an output. The system still further includes a processor for processing the output to obtain information related to the end surface of the part.

The actuator may be a motor-driven X-Y stage.

The at least one sensor may be a confocal sensor and/or a triangulation sensor.

The part may be threaded such as a threaded fastener having a recess in the end surface for accommodating a driver.

The threaded fastener may have a shank and the apparatus may releasably hold the shank of the threaded fastener.

The part may include a cartridge case having a mouth end and a primer end. The end surface may be located at the primer end and the information may include at least one of a split, a crack, flash hole presence, primer absence, a cocked primer, primer pocket diameter and an inverted primer.

The end surface may be located at the mouth end and the information may indicate at least one of a split, a fold, a dent, an out-of-round condition, inner diameter and outer diameter.

The beam may be a laser beam and the energy may be electromagnetic energy.

Still further in carrying out the above object and other objects of the present invention, a system for high-speed, high-resolution 3-D imaging of manufactured parts of various sizes at an imaging station having a measurement axis is provided. Each of the parts has a 3-D end surface and a length, a width and a part axis defined as being central to the part and parallel to its length. The system includes apparatus having a central axis substantially parallel to the measurement axis. The apparatus includes a plurality of members having open and closed positions. The members have holding faces which are substantially equidistant from the central axis during movement between the open and closed positions to align a part disposed between the holding faces at the station so that the part axis is substantially parallel with the measurement and central axes. The holding faces releasably hold the aligned part at a pair of spaced apart locations along the part axis. The system further includes an actuator for moving the apparatus so that the end surface moves in a plane substantially perpendicular to the measurement axis. The system still further includes a controller for controlling the actuator to move the end surface along a 2-D trajectory within the plane. The system further includes at least one sensor for emitting a beam of energy along the measurement axis onto the end surface during movement of the end surface along the 2-D trajectory to obtain reflected energy and for sensing at least a portion of the reflected energy to obtain an output. The system still further includes a processor for processing the output to obtain information related to the end surface of the part.

The above object and other objects, features, and advantages of the present invention are readily apparent from the following detailed description of the best mode for carrying out the invention when taken in connection with the accompanying drawings.

BRIEF DESCRIPTION OF THE DRAWINGS

FIG. 5 is a schematic block diagram view of a system constructed in accordance with at least one embodiment of the present invention and holding an aligned part;

FIG. 6 is a perspective schematic view, partially broken away, of a Z-axis sensor and self-centering holding apparatus (in an open position and without a held part) of the system of FIG. 5; and FIG. 7 is a dashed view illustrating a 2-D trajectory of a scanning beam of energy on a 3-D end surface of a part.

DETAILED DESCRIPTION OF THE PREFERRED EMBODIMENTS

Figure 1A:
FIGS. 1a and 1b are side and bottom schematic views, respectively, of a .50 caliber cartridge case.
Figure 1C:
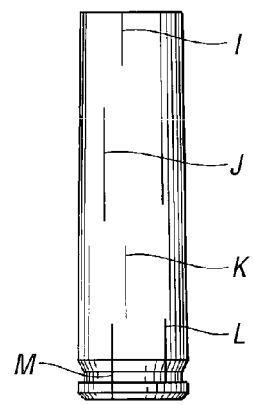
FIGS. 1c and 1d are side and bottom schematic views, respectively, of a .30 caliber cartridge case.
Figure 1B:
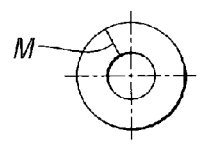
Figure 1D:
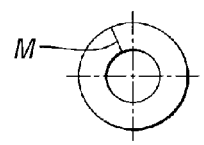
Figure 1E:
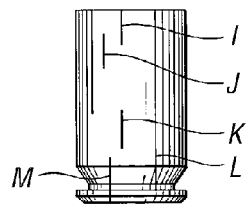
FIGS. 1e and 1f are side and bottom schematic views, respectively, of a .45 caliber cartridge case.
Figure 1F:
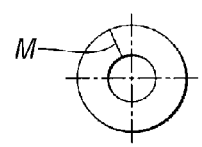
Figure 2:
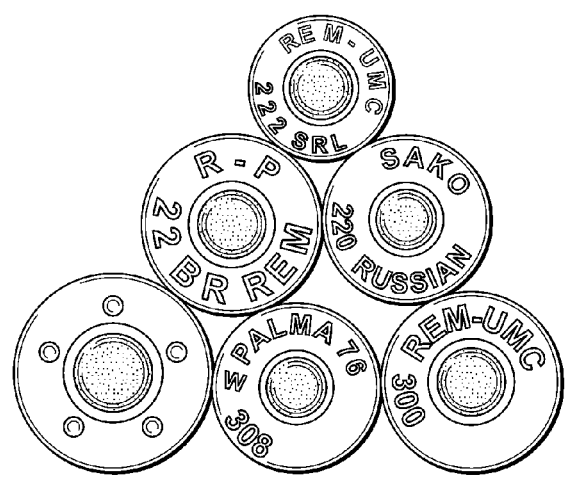
FIG. 2 is an end view of the primer ends of stacked cartridge cases capable of being imaged using at least one embodiment of the method and system of the present invention.
Figure 3:
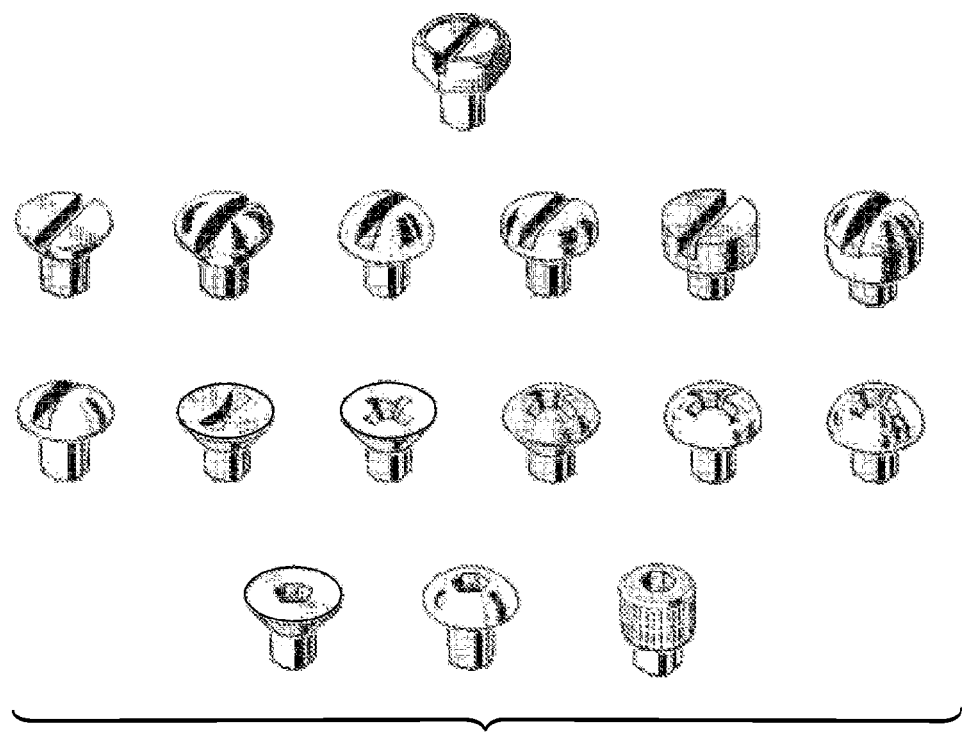
FIG. 3 is a perspective view, partially broken away, of a number of threaded fasteners including shanks and with their recessed heads capable of being imaged using at least one embodiment of the method and system of the present invention.

In general, one embodiment of the method and system of the present invention images 3-D end surfaces of manufactured parts of various sizes, such as cartridges and cartridge cases as illustrated in FIGS. 1a-1f and FIGS. 2 and 3-D end surfaces of threaded fasteners as illustrated in FIG. 3. The system is designed for high-speed, high-resolution imaging the 3-D end surfaces of small and medium caliber ammunition, as well as threaded fasteners. However, the system is also suitable for other small, mass-produced manufactured parts of various sizes where defects and 3-D dimensional issues occurring in end surfaces are of concern.

System Description

Referring now to FIG. 5, there is illustrated a non-contact system, generally indicated at 10, for inspecting parts, such as threaded fasteners, generally indicated at 24, (i.e. screws, bolts and the like), ammunition cartridge cases, gears and the like at an imaging station. The system 10 is especially designed to inspect parts having one or more 3-D end surfaces 28 and a length, a width and a part axis 11 defined as being central to the part 24 and parallel to its length. The part may be threaded and when the part is a threaded fastener it may have recess in the end surface for accommodating a driver as illustrated in FIG. 3. When the part is a cartridge case, typically the cartridge case has a mouth end and a primer end as illustrated in FIGS. 1a-2.

Typically, the system 10 includes a base 12 in the form of a granite block or an anti-vibration platform and a vertical support 14 mounted on the base 12. The system 10 also includes an X-Y positioning stage 16 on which there is supported apparatus, generally indicated at 18, including a vertical support 20 and one or more self-centering part holders, generally indicated at 22, mounted on the support 20 at spaced apart locations for holding a part whose 3-D end surface is to be imaged. As shown in FIG. 5, the upper part holder 22 may solely hold the threaded part 24 at a shank portion of the threaded fastener 24 typically when the part is relatively short in length. The lower part holder 22 may be required to align larger parts. Each of the part holders 22 is mounted on the support 20 for limited vertical movement along a Z-axis 25 (i.e. measurement axis) of the imaging station, as indicated by arrows 26. Typically, a pair of part holders 22 are provided for relatively long parts to properly align the part axis 11 of the part 24 in parallel with the measurement axis 25 for high-speed, high-resolution 3-D imaging of the 3-D end surface 28 of the part 24.

The system 10 also includes a motion controller 30 under control of a system control 32 to control the actuator or X-Y positioning stage 16 to move the end surface 28 along a 2-D trajectory within a plane 29 substantially perpendicular to the measurement and part axes 25 and 11, respectively, as illustrated in FIG. 7.

The system 10 also includes one or more Z-axis sensors 34 for emitting a beam of energy 46 along the measurement axis 25 substantially perpendicular to the plane 29 in which the end surface 28 moves. In this way, the beam of energy 46 scans the end surface 28 of the held part 24 to obtain reflected energy. The sensor 34 also typically senses at least a portion of the reflected energy to obtain an output which may be analog or digital. The one or more sensors are typically under control of the system control 32. The at least one Z-axis sensor 24 may be a triangulation-based laser sensor and/or a confocal laser sensor, as are well known in the art. Multiple Z-axis sensors may be provided since one particular type of Z-axis sensor may have deficiencies which the other Z-axis sensor does not have.

The at least one Z-axis sensor 34 is typically mounted on a horizontal support 35 which, in turn, is mounted on the vertical support 14 for limited vertical movement in the direction of arrows 36 along the Z-axis 25.

If the at least one Z-axis sensor 34 is a triangulation-based laser sensor and/or a confocal sensor, sensor signals may be acquired and processed at one or more signal processors 40 under control of the system control 32 to obtain sensor data which, in turn, is processed by at least one sensor data processor 42 to obtain information related to the end surface 28 of the part 24, such as defects and/or dimensions of the end surface 28, as indicated at block 44.

When the part is a cartridge case (FIGS. 1a-1f) having a mouth end and a primer end and the end surface is located at the primer end (FIG. 2), the information may indicate at least one of a split, a crack, flash hole presence, primer absence, a cocked primer, primer pocket diameter and an inverted primer. When the end surface is located at the mouth end of the cartridge case, the information may indicate at least one of a split, a fold, a dent, an out-of-round condition, inner diameter and outer diameter.

When the part is threaded, such as a threaded fastener 24 having a recessed end surface 28, as shown in FIGS. 3 and 5, a defect or dimension related to the end surface 28 is provided at block 44.

The data at block 42 is both acquired and processed under control of the system control 32 in accordance with a control algorithm. The data from the one or more sensors at block 34 are processed or fused, as indicated at block 40, for use with a measurement algorithm to thereby obtain information about the 3-D end surface 28 of the part 24.

When the at least one Z-axis sensor 34 is a triangulation-based laser sensor, the sensor 34 typically includes a laser and optical components (not shown) for transmitting the focused laser beam 46 incident on the end surface 28 of the part 24 from a first direction to obtain one or more reflected laser beams. The sensor 34 also typically includes at least one detector and preferably two detectors (not shown) positioned at an angle with respect to the laser beam 46 incident on the end surface 28 of the part 24. The sensor 34 is disposed to illuminate the part 24 with the focused beam 46 of laser energy. Analog signals from the detectors of the sensor 34 are received and processed at the block 40 under control of the system control 32 to obtain digital signals or data which are typically processed at the one or more sensor data processors 42.

Figure 4:
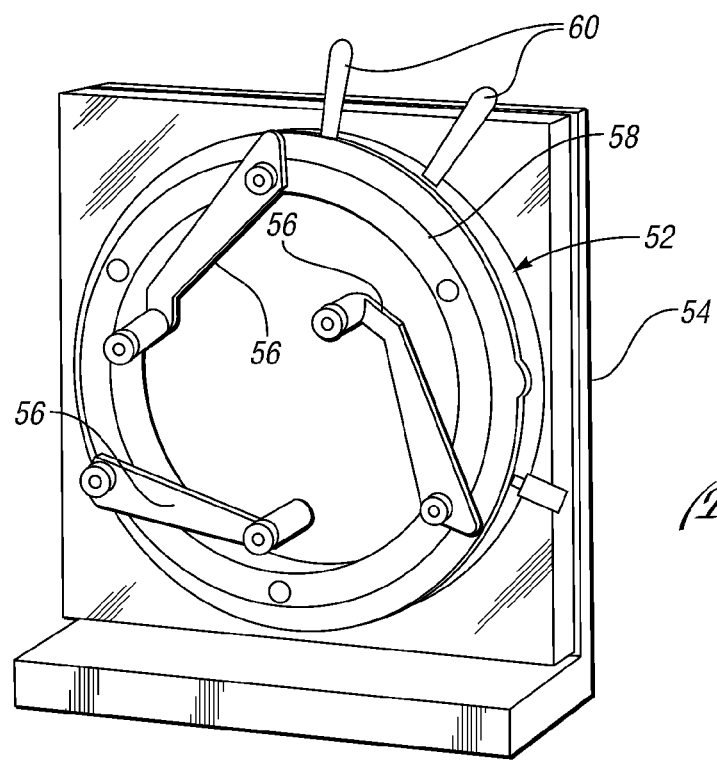
FIG. 4 is a perspective view of a prior art self-centering jaw clamp and kinematic mount or frame and available from Edmund Optics Inc. of Barrington, N.J., USA.

Each of the part holders 22 may be a self-centering part holder generally of the type as that generally indicated at 52 in FIG. 4. Other types of self-centering part holders, which are well known in the art, may also be used. The part holder 52, which is shown in its open position in FIG. 4, includes a frame 58 mounted on a base 54. The frame 52 is a kinematic mount which supports the self-centering apparatus 52 which includes three members or jaws 56 which are pivotally mounted on a ring member of the holder 52. Such a self-centering part holder and kinematic mount are available from Edmunds Optics Inc. of Barrington, N.J. As illustrated in FIG. 4, the holder 52 also includes a pair of lever arms 60, which in their rest, unactivated position allow the jaws 56 to hold a part therebetween in a holding position between the open and closed positions of the jaws 56. When the lever arms 60 are rotated relative to each other, the members 56 pivot away from any held part against the biasing action of one or more springs (not shown) contained within the holder 52 to release the part.

Referring now to FIG. 6, the self-centering part holder 22 of the system 10 is similar to the part holder of FIG. 4, except the part holder 22 has a pair of annular members which rotate relative to one another against the biasing action of one or more springs (not shown) when lever arms 70 connected to their annular members rotate relative to one another. The one or more springs of the part holder 22 normally bias pivotable members 72 towards their closed position from their open position to align and hold a part in a central recess 74. After a part has been positioned between the members 72, the lever arms 70 are released so that the members 72 can initially align and then hold the part 24 centrally positioned within the central recess 74. In this way, the part axis 11 is aligned to be substantially parallel to a central axis 75 of at least one of the holders 22. The central axis 75 is substantially parallel to the measurement axis 25.

Each self-centering part holder 22 is mounted on the common vertical support 20 by a horizontally extending support 76. Each horizontal support 76 is mounted on the vertical support 20 for limited vertical movement, as indicated by the arrows 26 in FIG. 5, by a manual adjustment mechanism 78.

In one embodiment of the present invention, the one or more Z-axis sensors 34, the X-Y positioning stage 16, the base 12, the one or more signal processors 40, the one or more sensor data processors 42, the system control 32 and the motion controller 30 are provided by B&H Machine Company of Roberts, Wis. 45023. Such a system is described by B&H Machine Company as a non-contact surface measurement system or surface profiler. Such a system includes a PC-based control system. The sensor(s) for the Z-axis can be a laser triangulation sensor and/or a confocal sensor.

While exemplary embodiments are described above, it is not intended that these embodiments describe all possible forms of the invention. Rather, the words used in the specification are words of description rather than limitation, and it is understood that various changes may be made without departing from the spirit and scope of the invention. Additionally, the features of various implementing embodiments may be combined to form further embodiments of the invention.

What is claimed is:

1. A method of high-speed, high-resolution 3-D imaging of manufactured parts of various sizes at an imaging station having a measurement axis, each of the parts having a 3-D end surface and a length, a width and a part axis defined as being central to the part and parallel to its length, the method comprising:
aligning a part to be imaged at the station so that the part axis is substantially parallel with the measurement axis;
releasably holding the aligned part;
scanning the end surface of the held part with a beam of energy along the measurement axis to obtain reflected energy;
sensing at least a portion of the reflected energy to obtain an output;
processing the output to obtain information related to the end surface of the part; and
generating control signals to control the step of scanning.

2. The method as claimed in claim 1 wherein the step of scanning includes the steps of:
directing the beam of energy along the measurement axis; and
controllably moving the end surface relative to the beam along a 2-D trajectory in a plane substantially perpendicular to the part axis wherein the part axis is substantially perpendicular to the plane during the step of scanning.

3. The method as claimed in claim 1 wherein the part is threaded.

4. The method as claimed in claim 3 wherein the part is a threaded fastener having a recess in the end surface for accommodating a driver.

5. The method as claimed in claim 4 wherein the threaded fastener has a shank and wherein the shank of the fastener is releasably held during the step of holding.

6. The method as claimed in claim 1 wherein the part includes a cartridge case having a mouth end and a primer end.

7. The method as claimed in claim 6 wherein the end surface is located at the primer end and wherein the information indicates at least one of a split, a crack, flash hole presence, primer absence, a cocked primer, primer pocket diameter, and an inverted primer.

8. The method as claimed in claim 6 wherein the end surface is located at the mouth end and wherein the information indicates at least one of a split, a fold, a dent, an out-of-round condition, inner diameter and outer diameter.

9. The method as claimed in claim 1 wherein the beam is a laser beam and the energy is electromagnetic energy.

10. The method as claimed in claim 9 wherein the step of sensing is performed with a triangulation-based sensor.

11. The method as claimed in claim 9 wherein the step of sensing is performed with a confocal sensor.

12. A system for high-speed, high-resolution 3-D imaging of manufactured parts of various sizes at an imaging station having a measurement axis, each of the parts having a 3-D end surface and a length, a width and a part axis defined as being central to the part and parallel to its length, the system comprising:
apparatus having a central axis substantially parallel to the measurement axis and including a plurality of members having open and closed positions, the members having holding faces which are substantially equidistant from the central axis during movement between the open and closed positions to align a part disposed between the holding faces at the station so that the part axis is substantially parallel with the measurement and central axes, the holding faces releasably holding the aligned part in a holding position between the open and closed positions;
an actuator for moving the apparatus so that the end surface moves in a plane substantially perpendicular to the measurement axis;
a controller for controlling the actuator to move the end surface along a 2-D trajectory within the plane;
at least one sensor for emitting a beam of energy along the measurement axis onto the end surface during movement of the end surface along the 2-D trajectory to obtain reflected energy and for sensing at least a portion of the reflected energy to obtain an output; and
a processor for processing the output to obtain information related to the end surface of the part.

13. The system as claimed in claim 12 wherein the actuator is a motor-driven X-Y stage.

14. The system as claimed in claim 12 wherein the sensor is a confocal sensor.

15. The system as claimed in claim 12 wherein the sensor is a triangulation sensor.

16. The system as claimed in claim 12 wherein the part is threaded.

17. The system as claimed in claim 16 wherein the part is a threaded fastener having a recess in the end surface for accommodating a driver.

18. The system as claimed in claim 17 wherein the threaded fastener has a shank and wherein the apparatus releasably holds the shank of the threaded fastener.

19. The system as claimed in claim 12 wherein the part includes a cartridge case having a mouth end and a primer end.

20. The system as claimed in claim 19 wherein the end surface is located at the primer end and wherein the information includes at least one of a split, a crack, flash hole presence, primer absence, a cocked primer, primer pocket diameter and an inverted primer.

21. The system as claimed in claim 19 wherein the end surface is located at the mouth end and wherein the information indicates at least one of a split, a fold, a dent, an out-of-round condition, inner diameter and outer diameter.

22. The system as claimed in claim 12 wherein the beam is a laser beam and the energy is electromagnetic energy.

23. A system for high-speed, high-resolution 3-D imaging of manufactured parts of various sizes at an imaging station having a measurement axis, each of the parts having a 3-D end surface and a length, a width and a part axis defined as being central to the part and parallel to its length, the system comprising:
apparatus having a central axis substantially parallel to the measurement axis and including a plurality of members having open and closed positions, the members having holding faces which are substantially equidistant from the central axis during movement between the open and closed positions to align a part disposed between the holding faces at the station so that the part axis is substantially parallel with the measurement and central axes, the holding faces releasably holding the aligned part at a pair of spaced apart locations along the part axis;
an actuator for moving the apparatus so that the end surface moves in a plane substantially perpendicular to the measurement axis;
a controller for controlling the actuator to move the end surface along a 2-D trajectory within the plane;

at least one sensor for emitting a beam of energy along the measurement axis onto the end surface during movement of the end surface along the 2-D trajectory to obtain reflected energy and for sensing at least a portion of the reflected energy to obtain an output; and a processor for processing the output to obtain information related to the end surface of the part.

* * * * *